US009709696B2

(12) United States Patent
Price et al.

(10) Patent No.: US 9,709,696 B2
(45) Date of Patent: **\*Jul. 18, 2017**

(54) INTENSITY-INDEPENDENT OPTICAL COMPUTING DEVICE

(71) Applicant: Halliburton Energy Services, Inc., Houston, TX (US)

(72) Inventors: James M. Price, The Woodlands, TX (US); David L. Perkins, The Woodlands, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/911,361

(22) PCT Filed: Oct. 16, 2013

(86) PCT No.: PCT/US2013/065291
§ 371 (c)(1),
(2) Date: Feb. 10, 2016

(87) PCT Pub. No.: WO2015/057219
PCT Pub. Date: Apr. 23, 2015

(65) Prior Publication Data
US 2016/0187531 A1    Jun. 30, 2016

(51) Int. Cl.
*G01J 4/00* (2006.01)
*G01V 8/20* (2006.01)
(Continued)

(52) U.S. Cl.
CPC .............. *G01V 8/20* (2013.01); *E21B 49/081* (2013.01); *G01J 4/02* (2013.01); *G01N 21/21* (2013.01);
(Continued)

(58) Field of Classification Search
CPC .... G01N 21/21; G01J 4/00; G01J 4/04; G01J 4/02; G01B 11/18
(Continued)

(56) References Cited

U.S. PATENT DOCUMENTS 6,067,157 A    5/2000 Altendorf
6,520,056 B1 *  2/2003 Nemeth .................. B26D 5/00
                                              250/225
(Continued)

FOREIGN PATENT DOCUMENTS

FR          2393296 A1    12/1978
WO    WO 2006/052644 A2    5/2006
(Continued)

OTHER PUBLICATIONS

International Search Report and the Written Opinion of the International Searching Authority, or the Declaration, Mar. 19, 2014, PCT/US2013/065291, 17 pages, ISA/US.
(Continued)

*Primary Examiner* — Tarifur Chowdhury
*Assistant Examiner* — MD M Rahman
(74) *Attorney, Agent, or Firm* — Haynes and Boone, LLP

(57) ABSTRACT

An intensity-independent optical computing device and method for performing multivariate optical computing based on changes in polarization of the reflected and/or transmitted electromagnetic radiation to thereby determine sample characteristics.

33 Claims, 5 Drawing Sheets

(51) Int. Cl.
*G01N 21/21* (2006.01)
*E21B 49/08* (2006.01)
*G01J 4/02* (2006.01)
*G02B 1/02* (2006.01)

(52) U.S. Cl.
CPC ....... *G02B 1/02* (2013.01); *G01N 2201/0683* (2013.01); *G01N 2201/12* (2013.01)

(58) Field of Classification Search
USPC ........................................................ 356/364
See application file for complete search history.

(56) References Cited

U.S. PATENT DOCUMENTS

| | | | |
|---|---|---|---|
| 7,193,711 B2 | 3/2007 | Rassman et al. | |
| 7,233,396 B1 | 6/2007 | Hall et al. | |
| 7,251,029 B2 | 7/2007 | Kishikawa et al. | |
| 2002/0179301 A1* | 12/2002 | Schultz | E21B 47/01 166/250.01 |
| 2003/0197864 A1 | 10/2003 | Wei et al. | |
| 2007/0177240 A1* | 8/2007 | Van Beek | A61B 5/14532 359/196.1 |
| 2008/0246948 A1 | 10/2008 | Van Schaik et al. | |
| 2009/0051916 A1 | 2/2009 | Otani et al. | |
| 2010/0265509 A1 | 10/2010 | Jones et al. | |
| 2011/0051143 A1* | 3/2011 | Flanders | G01B 9/02004 356/451 |
| 2013/0033702 A1 | 2/2013 | Tunheim et al. | |
| 2013/0044318 A1 | 2/2013 | Cho et al. | |
| 2013/0084079 A1 | 4/2013 | Nordholt et al. | |
| 2015/0002852 A1* | 1/2015 | de Groot | G01B 9/0209 356/491 |

FOREIGN PATENT DOCUMENTS

| | | |
|---|---|---|
| WO | WO 2008/042866 A2 | 4/2008 |
| WO | WO 2012/108885 A1 | 8/2012 |

OTHER PUBLICATIONS

European Search Report, Mar. 29, 2017, EP 13895463, 8 pages.

* cited by examiner

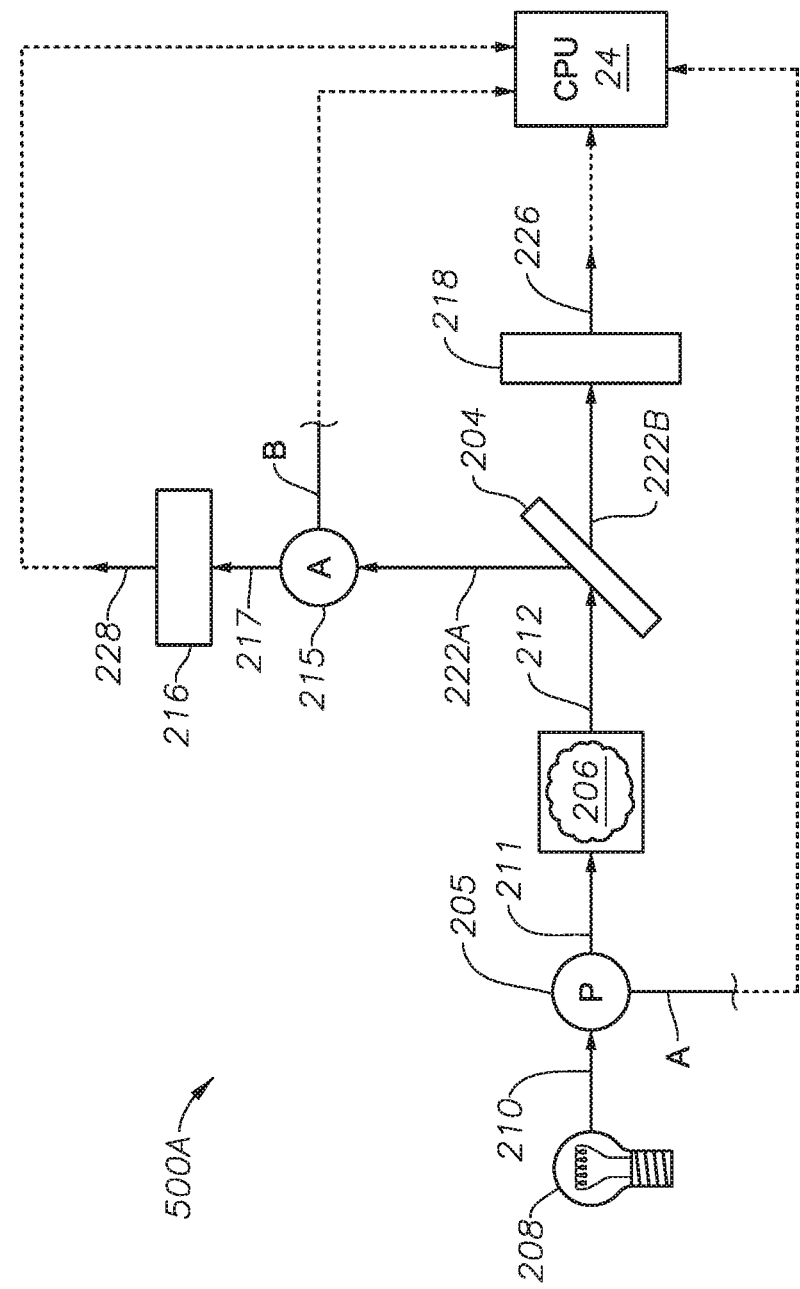

INTENSITY-INDEPENDENT OPTICAL COMPUTING DEVICE

The present application is a U.S. National Stage patent application of International Patent Application No. PCT/US2013/065291, filed on Oct. 16, 2013, the benefit of which is claimed and the disclosure of which is incorporated herein by reference in its entirety.

FIELD OF THE DISCLOSURE

The present disclosure relates generally to optical sensors and, more specifically, to an intensity-independent optical sensor that analyzes changes in electromagnetic polarization states to determine sample characteristics.

BACKGROUND

In recent years, optical computing techniques have been developed for applications in the oil and gas Industry in the form of optical sensors on downhole or surface equipment to evaluate a variety of fluid properties. In general, an optical computing device is a device configured to receive an input of electromagnetic radiation from a sample and produce an output of electromagnetic radiation from a processing element, also referred to as an optical element, wherein the output reflects the measured intensity of the electromagnetic radiation. The optical element may be, for example, a narrow band optical element or an Integrated Computational Element ("ICE") (also known as a Multivariate Optical Element ("MOE").

Fundamentally, optical computing devices utilize optical elements to perform calculations, as opposed to the hardwired circuits of conventional electronic processors. When light from a light source interacts with a substance, unique physical and chemical information about the substance is encoded in the electromagnetic radiation that is reflected from, transmitted through, or radiated from the sample. Thus, the optical computing device, through use of the ICE core and one or more detectors, is capable of extracting the information of one or multiple characteristics/properties or analytes within a substance and converting that information into a detectable output signal reflecting the overall properties of a sample. Such characteristics may include, for example, the presence of certain elements, compositions, fluid phases, etc. existing within the substance.

Therefore, traditional optical computing devices analyze the measured intensity of sample-interacted radiation in order to determine a sample characteristic of interest. In other words, traditional computing devices are intensity-dependent. As a result, traditional computing devices in some instances can be limited in a number of ways. First, for example, such devices may have a spectral range covering a low absorbing region of the analyte. Second, only one observable, wavelength-dependent variable per analyte is measured. Third, in some cases, elaborate calibration schemes may be needed to correct for radiometric effects. Fourth, such devices can have sensitivity issues resulting from low or fluctuating light intensities and scattering.

Accordingly, there is a need in the art for an intensity-independent optical computing device useful to detect and monitor sample characteristic data in a desired environment.

BRIEF DESCRIPTION OF THE DRAWINGS

FIGS. 5A and 5B are block diagrams of yet other intensity-independent optical computing devices employing a dual detector geometry, according to certain illustrative embodiments of the present disclosure.

DESCRIPTION OF ILLUSTRATIVE EMBODIMENTS

Illustrative embodiments and related methodologies of the present disclosure are described below as they might be employed in an intensity-independent optical computing device. In the interest of clarity, not all features of an actual implementation or methodology are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various embodiments and related methodologies of the disclosure will become apparent from consideration of the following description and drawings.

Illustrative embodiments and related methodologies of the present disclosure are directed to an intensity-independent optical computing device and method for performing multivariate optical computing based on the change in polarization of the reflected and/or transmitted electromagnetic radiation to thereby determine sample characteristics. In general, the illustrative optical computing devices include two polarizers, an optical element, and a detector. The first polarizer defines a first polarization state of light by transforming unpolarized light from an electromagnetic source into linearly polarized light wherein the P and S components are in phase. The subsequent reflection and/or transmission of the light through the sample and optical element will transform the polarization from linear to elliptical wherein the P and S components are out of phase. The second polarizer receives the out of phase light, and optically interacts therewith to generate light in a second polarization state. The detector converts the light intensity to an electronic output signal that is utilized by a processor, along with an analysis of the change in polarization between the first and second polarization states and the angular orientations of the polarizers, to determine a sample characteristic of interest. Accordingly, through use of the polarizers, the change in polarization can be determined and then utilized to determine one or more sample characteristics of interest.

Figure 1:
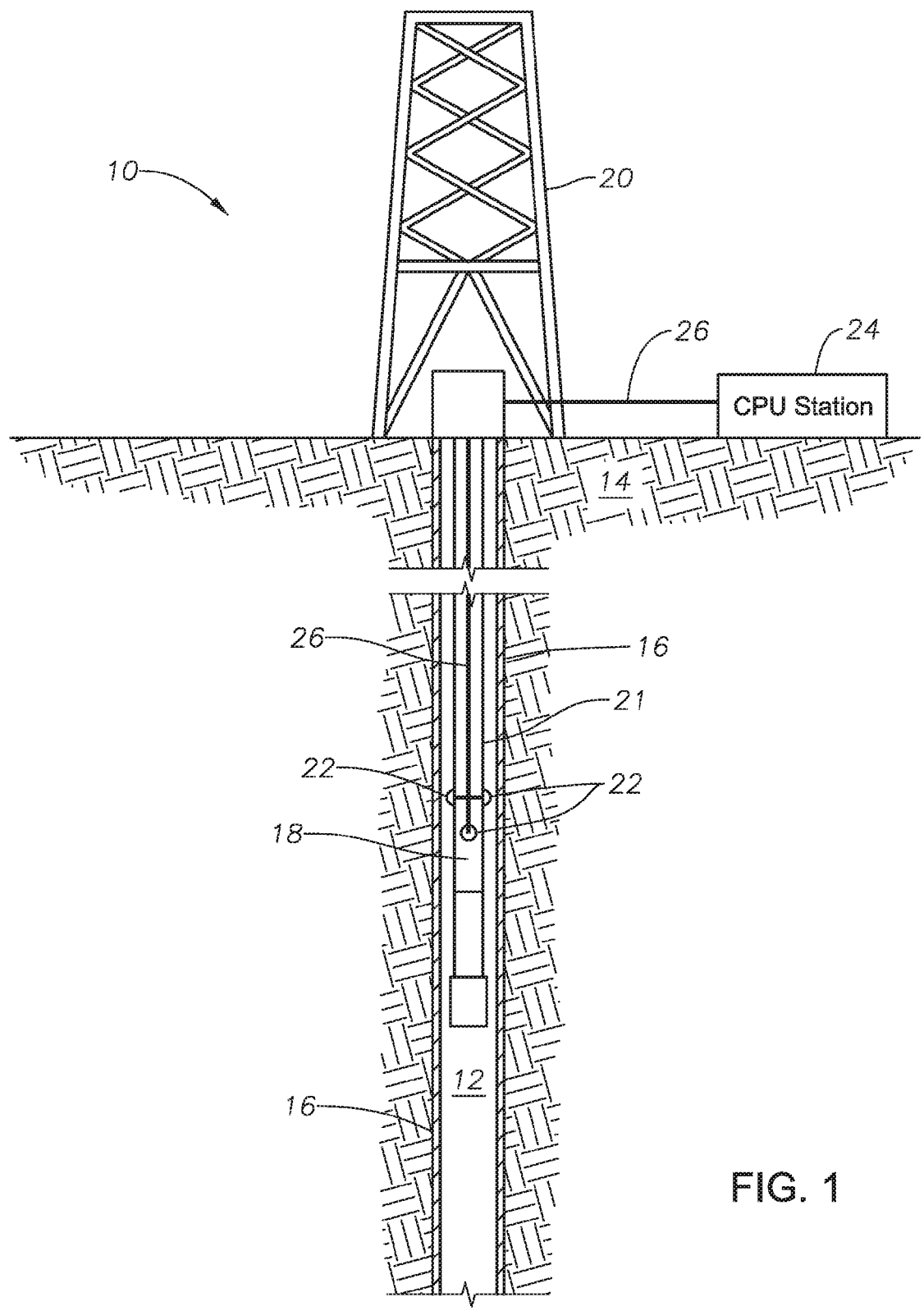
FIG. 1 illustrates a well system having intensity-independent optical computing devices deployed therein for sample characteristic detection according to certain illustrative embodiments of the present invention.

Although the optical computing devices described herein may be utilized in a variety of environments, the following description will focus on downhole well applications. FIG. 1 illustrates a plurality of optical computing devices 22 positioned along a workstring 21 extending along a downhole well system 10 according to certain illustrative embodiments of the present disclosure. Workstring 21 may be, for example, a wireline assembly, logging-while-drilling assembly, measuring-while drilling assembly, production string or other drilling assembly. Well system 10 comprises a vertical wellbore 12 extending down into a hydrocarbon reservoir 14 (although not illustrated, wellbore 12 may also comprise one or more lateral sections). Wellbore equipment 20 is positioned atop vertical wellbore 12, as understood in the art. Wellbore equipment may be, for example, a blow out preventer, derrick, floating platform, etc. As understood in the art, after vertical wellbore 12 is formed, tubulars 16 (casing, for example) are extended therein to complete wellbore 12.

One or more optical computing devices 22 may be positioned along wellbore 12 at any desired location. In certain embodiments, optical computing devices 22 are positioned along the internal or external surfaces of downhole tool 18 (as shown in FIG. 1) which may be, for example, intervention equipment, surveying equipment, or completion equipment including valves, packers, screens, mandrels, gauge mandrels, in addition to casing or tubing tubulars/joints as referenced below. Alternatively, however, optical computing devices 22 may be permanently or removably attached to tubulars 16 and distributed throughout wellbore 12 in any area in which sample characteristic detection/monitoring is desired. Optical computing devices 22 may be coupled to a remote power supply (located on the surface or a power generator positioned downhole along the wellbore, for example), while in other embodiments each optical computing device 22 comprises an on-board battery. Moreover, optical computing devices 22 are communicably coupled to a CPU station 24 via a communications link 26, such as, for example, a wireline or other suitable communications link. Those ordinarily skilled in the art having the benefit of this disclosure will readily appreciate that the number and location of optical computing devices 22 may be manipulated as desired.

In certain embodiments, optical computing devices 22 comprise an ICE core that optically interacts with a sample of interest (wellbore fluid, downhole tool component, tubular, for example) to determine the sample characteristic. Illustrative characteristics include the presence and quantity of specific inorganic gases such as, for example, $CO_2$ and $H_2S$, organic gases such as methane (C1), ethane (C2) and propane (C3, saline water, dissolved ions (Ba, Cl, Na, Fe, or Sr, for example), or various other characteristics (p.H., density and specific gravity, viscosity, total dissolved solids, sand content, etc.). In certain embodiments, a single optical computing device 22 may detect a single characteristic, while in others a single optical computing device 22 may determine multiple characteristics, as will be understood by those ordinarily skilled in the art having the benefit of this disclosure.

CPU station 24 comprises a signal processor (not shown), communications module (not shown) and other circuitry necessary to achieve the objectives of the present disclosure, as will be understood by those ordinarily skilled in the art having the benefit of this disclosure. In addition, it will also be recognized that the software instructions necessary to carry out the objectives of the present disclosure may be stored within storage located in CPU station 24 or loaded into that storage from a CD-ROM or other appropriate storage media via wired or wireless methods. Communications link 26 provides a medium of communication between CPU station 24 and optical computing devices 22. Communications link 26 may be a wired link, such as, for example, a wireline or fiber optic cable extending down into vertical wellbore 12. Alternatively, however, communications link 26 may be a wireless link, such as, for example, an electromagnetic device of suitable frequency, or other methods including acoustic communication and like devices.

In certain illustrative embodiments, CPU station 24, via its signal processor, controls operation of each optical computing device 22. In addition to sensing operations, CPU station 24 may also control activation and deactivation of optical computing devices 22. Optical computing devices 22 each include a transmitter and receiver (transceiver, for example) (not shown) that allows bi-directional communication over communications link 26 in real-time. In certain illustrative embodiments, optical computing devices 22 will transmit all or a portion of the sample characteristic data to CPU station 24 for further analysis. However, in other embodiments, such analysis is completely handled by each optical computing device 22 and the resulting data is then transmitted to CPU station 24 for storage or subsequent analysis. In either embodiment, the processor handling the computations analyzes the characteristic data and, through utilization of Equation of State ("EOS") or other optical analysis techniques, derives the characteristic indicated by the transmitted data, as will be readily understood by those ordinarily skilled in the art having the benefit of this disclosure.

Figure 2:
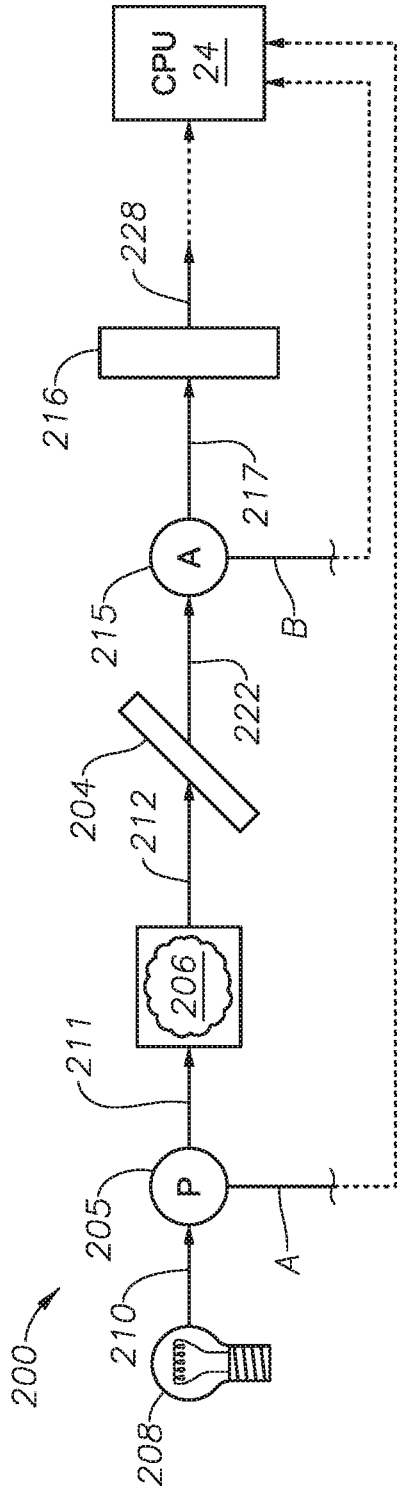
FIG. 2 is a block diagram of an intensity-independent optical computing device employing a transmission mode design for sample characteristic detection, according to certain illustrative embodiments of the present disclosure.

FIG. 2 is a block diagram of an intensity-independent optical computing device 200 employing a transmission mode design, according to certain illustrative embodiments of the present disclosure. An electromagnetic radiation source 208 may be configured to emit or otherwise generate electromagnetic radiation 210. As understood in the art, electromagnetic radiation source 208 may be any device capable of emitting or generating electromagnetic radiation. For example, electromagnetic radiation source 208 may be a light bulb, light emitting device, laser, blackbody, photonic crystal, or X-Ray source, etc. In certain embodiments, the spectrum of electromagnetic radiation is not restricted to near infrared ("IR") (750-1500 nm) or IR (>1500 nm), but may also extend into the visible (250-750 nm), mid-UV (190-250 nm), and far UV (140-190 nm), for example.

As shown in FIG. 2, electromagnetic radiation 210 is directed to optically interact with a first polarizer 205. As will be understood by those ordinarily skilled in the art having the benefit of this disclosure, a polarizer is a filter that only transmits a certain amount of light dependent upon its polarization setting. Therefore, once interacted with first polarizer 205, electromagnetic radiation 210 becomes linearly polarized to thereby produce first polarized light 211. Linear polarization refers to the state wherein the P and S components are in phase. Here, first polarizer 205 only allows a preferred electric field orientation to be transmitted through it, thereby defining a given orientation (P, S or some intermediate P&S) and phase. Thus, first polarizer 205 defines the polarization state (i.e., first polarization state) of electromagnetic radiation 210. As will be discussed below, first polarizer 205 is coupled to CPU station 24 (or an on-board processor) via link A, whereby CPU station 24 sends a signal to first polarizer 205 to thereby define the first polarization state by manipulating the angular orientation of polarizer 205.

First polarized light 211 then optically interacts with sample 206 (wellbore fluid flowing through wellbores 12, for example) to thereby generate sample-interacted light 212. Sample 206 may be any fluid (liquid or gas), solid substance or material such as, for example, downhole tool components, tubulars, rock formations, slurries, sands, muds, drill cuttings, concrete, other solid surfaces, etc. In this specific embodiment, however, sample 206 is a multi-phase wellbore fluid (comprising oil, gas, water, solids, for example) consisting of a variety of fluid characteristics such as, for example, C1-C4 and higher hydrocarbons, groupings of such elements, and saline water. As a result of interacting with sample 206, first polarized light 211 transforms from linearly polarized to elliptically polarized, resulting in sample-interacted light 212.

Sample 206 may be provided to optical computing device 200 through a flow pipe or sample cell, for example, containing sample 206, whereby it is introduced to first polarized light 211. Alternatively, optical computing device 200 may utilize an optical configuration consisting of an internal reflectance element which analyzes the wellbore fluid as it flows thereby. While FIG. 2 shows first polarized light 211 as passing through or incident upon the sample 206 to produce sample-interacted light 212 (i.e., transmission or fluorescent mode), it is also contemplated herein to reflect first polarized light 211 off of the sample 206 (i.e., reflectance mode), such as in the case of a sample 206 that is translucent, opaque, or solid, and equally generate the sample-interacted light 212.

After being illuminated with first polarized light 211, sample 206 containing an analyte of interest (a characteristic of the sample, for example) produces an output of electromagnetic radiation (sample-interacted light 212, for example) which contains spectral information that corresponds to sample characteristics. Sample-interacted light 212 is then directed to one or more optical elements 204 to produce optically-interacted light 222. As a result of interacting with optical element 204, optically-interacted light 222 has a different state of polarization than sample-interacted light 212.

Optical element 204 may be a variety of optical elements such as, for example, one or more narrow band optical filters or ICE cores arranged or otherwise used in series in order to determine the characteristics of sample 206. In those embodiments using ICE cores, the ICE core may be configured to be associated with a particular characteristic of sample 206 or may be designed to approximate or mimic the regression vector of the characteristic in a desired manner, as would be understood by those ordinarily skilled in the art having the benefit of this disclosure. Additionally, in an alternative embodiment, optical element 204 may function as both a beam splitter and computational processor, as will be understood by those same ordinarily skilled persons.

More specifically, in those embodiments utilizing ICE cores as optical element 204, the ICE core is designed and fabricated to match a regression vector that produces a desired change in polarization needed to measure the analyte of interest. Such ICE cores are different from traditional ICE cores that are designed to match a regression vector that produces the desired intensity profile needed to measure the analyte of interest. Nevertheless, certain illustrative ICE cores utilized in the present disclosure may be more efficiently designed since the polarization phase may be periodic with quarter-wavelength increments and allows for a desired polarization state to be achieved by tracing the line integral along the preferred Poincare sphere. Moreover, other illustrative ICE cores may be oriented at a specified angle of incidence such that the detection sensitivity and accuracy is optimized with respect to its design.

Referring back to FIG. 2, optically interacted light 222, which is elliptically polarized and related to the characteristic or analyte of interest, is conveyed to second polarizer 215 where it optically interacts to produce second polarized light 217. Here, second polarizer 215 (more commonly referred to as an analyzer) defines a second polarization state of optically-interacted light 222 that represents a change in polarization between first and second polarized lights 211, 217. As with first polarizer 205, second polarizer 215 only allows a defined amount of light to transmit through dependent upon its polarization setting (i.e., angular orientation).

Second polarized light 217 is then directed to detector 216 for analysis and quantification. Here, detector 216 converts the intensity of second polarized light 217 into an electronic signal 228 that is used by CPU station 24 to determine the sample characteristic of interest. To do so, CPU station 24 compares the change in polarization between the first and second polarization states, as well as the angular orientations of first and second polarizers 205,215. As shown in FIG. 2, CPU station 24 is coupled to polarizers 205,215, via links A and B to thereby receive data reflecting the first and second polarization states and to allow CPU station 24 to control the angular orientations of the first and second polarizers 205, 215. As a result, output signal 228 will also be a function of the angles of first and second polarizers 205,215. As will be described in more detail below, CPU station 24 then utilizes output signal 228 and the data reflecting the polarization states and angular orientations received via links A and B to determine the characteristics of interest.

Detector 216 may be any device capable of detecting electromagnetic radiation, and may be generally characterized as an optical transducer. For example, detector 216 may be, but is not limited to, a thermal detector such as a thermopile or photoacoustic detector, a semiconductor detector, a piezo-electric detector, charge coupled device detector, video or array detector, split detector, photon detector (such as a photomultiplier tube), photodiodes, and/or combinations thereof, or the like, or other detectors known to those ordinarily skilled in the art. Detector 216 is further configured to produce the output signal 228 in the form of a voltage or current that corresponds to the intensity of second polarized light 217. In at least one embodiment, output signal 228 produced by detector 216 and the concentration of the characteristic of the sample 206 may be directly proportional. In other embodiments, the relationship may be a polynomial function, an exponential function, and/or a logarithmic function.

As previously described, ultimately, CPU station 24 (or a processor on-board device 200) analyzes the change in spectral information (between first and second polarization states), and the angles of first and second polarizers 205,215, to derive the desired sample characteristic. To do so, CPU station 24 utilizes second polarized light 217 incident on detector 216 to determine the reflected and/or transmitted polarization (i.e., second polarization state), which is compared with the known incident polarization at first polarizer 205 (determined via link A) to thereby determine the change in amplitude and phase of the polarization due to the interaction with sample 206 and optical element 204. This data, along with the angles of first and second polarizers 205,215, is then utilized to determine the desired sample characteristics. As described above, CPU station 24 defines the second polarization state by controlling the angle of second polarizer 215 via link B.

A more detailed description of illustrative computations used by CPU station 24 to determine the sample characteristic will now be described. To measure the change in polarization states, CPU station 24 may define the phase difference between the P and S components of the incoming first polarized light 211 and outgoing second polarized light 217 reflected electric field vectors as δ1 and δ2, respectively. Therefore, the change in phase difference in polarization that occurs between first polarizer 205 (i.e., first polarization state) and upon interacting with sample 206 and optical element 204 (i.e., second polarization state) is represented by:

$$\Delta = \delta 1 - \delta 2 \qquad \text{Eq. (1).}$$

Additionally, the amplitude of the polarization will also change upon transmission. If $T_p$ and $T_s$ are the ratio of the transmitted wave amplitude to the incident wave amplitude for the P and S components, respectively, then Ψ can be defined such that:

$$\text{Tan } \Psi = |T_p/T_s| \qquad \text{Eq. (2)}$$

is the angle whose tangent is the ratio of the magnitudes of the total transmission coefficient. Accordingly, CPU station 24 defines Ψ and Δ as the measured parameters describing the change in polarization between the first polarized state of electromagnetic radiation 211 and the incident light upon interaction with sample 206 and optical element 204 (i.e., second polarized state reflected in second polarized light 217). Note also here that one of the advantages of the present disclosure is the calculation of two measured wavelength dependent variables Ψ and Δ, as opposed to only one wavelength dependent variable (intensity) as with traditional intensity-dependent optical computing devices. Moreover, as will be understood by those ordinarily skilled in the art having the benefit of this disclosure, the foregoing also holds true for embodiments utilizing reflection upon replacing $T_p$ and $T_s$ with $R_p$ and $R_s$ in Equation 2.

In addition, the design of optical element 204 is one that would target a regression vector that matches Ψ and/or Δ in order to measure the analyte concentration (i.e., sample characteristic). As previously described, optical element 204 may be one or more ICE cores such as, for example, those utilized in traditional optical computing devices. In certain alternative illustrative embodiments, the ICE cores may also incorporate one or more thin film layers made of birefringent materials. As known to those skilled in the art having the benefit of this disclosure, birefringent materials are optically anisotropic materials whose refractive index depends on the state of polarization and the direction of propagation of electromagnetic radiation (e.g., light) transmitted through the material.

As will further be understood by those ordinarily skilled in the art having the benefit of this disclosure, the multiple layers of the illustrative ICE cores described herein exhibit different refractive indices. By properly selecting the materials of each layer and their relative thickness and spacing, the ICE core may be configured to selectively pass/reflect/refract predetermined fractions of electromagnetic radiation at different wavelengths. Each wavelength is given a predetermined weighting or loading factor. The thickness and spacing of the layers may be determined using a variety of approximation methods from the spectrum of the characteristic or analyte of interest. These methods may include inverse Fourier transform ("IFT") of the optical transmission spectrum and structuring the ICE core as the physical representation of the IFT. The approximations convert the IFT into a structure based on known materials with constant refractive indices.

The weightings that the layers of the ICE core apply at each wavelength may be set to the regression weightings described with respect to a known equation, data, or spectral signature. When electromagnetic radiation interacts with a substance, unique physical and chemical information about the substance may be encoded in the electromagnetic radiation that is reflected from, transmitted through, or radiated from the substance. This information is often referred to as the spectral "fingerprint" of the substance. The ICE core may be configured to perform the dot product of the received electromagnetic radiation and the wavelength dependent transmission function of the ICE core. The wavelength dependent transmission function of the ICE core is dependent on the layer material refractive index, the number of layers and thickness of each layer. The ICE core transmission function is then analogous to a desired regression vector derived from the solution to a linear multivariate problem targeting a specific component of the substance being analyzed. As a result, the output change in polarization (Ψ and Δ) of the optical element 204 is related to (e.g., directly proportional to) the characteristic or analyte of interest of the sample 206.

Therefore, referring back to FIG. 2, output signal 228 will be a function of the angles of polarizer 205,215, as well as the characteristics (Ψ and/or Δ) of sample 206 and optical element 204. Because the angles of first and second polarizers 205,215 are known input parameters (known via links A,B), CPU station 24 can solved for Ψ and/or Δ as described above. For example, using a continuously rotating second polarizer 215 (angle=A): The light intensity, I, is proportional to:

$$m \cdot \cos(2A) + n \cdot \sin(2A) \qquad \text{Eq. (3),}$$

where m and n are functions of Ψ, Δ and the polarizer angle, P. A Fourier decomposition of the signal with regards to the known angle A will allow CPU station 24 to determine Ψ and Δ.

To further illustrate the theory behind the illustrative embodiments of the present disclosure, note that the intensity, I, at detector 216 is proportional to the squared modulus of the electric field vector, E, of the output beam (second polarized light 217), and can be represented as $I \alpha |E|^2$. In the illustrative embodiment of FIG. 2, for example, the electric field is a product of the Jones Matrix for each optical element within the beam path and can be expressed as:

$$E = [A] \cdot [ICE] \cdot [\text{sample}] \cdot [P] \cdot [\text{source}] \qquad \text{Eq. (4),}$$

where A is second polarizer 215, ICE is optical element 204, sample is sample 206, P is first polarizer 205, and source is electromagnetic radiation source 208. Formulas for each element's Jones Matrix are known in the art.

For other configurations, however, the product for each optical element matrix is traced from the detector back to the source. In one example, for a rotating analyzer configuration with P-polarized light exiting the polarizer and incident on a sample, the respective Jones Matrices are:

$$\text{Source} = \begin{bmatrix} E_P e^{i\delta} \\ E_S e^{i\delta} \end{bmatrix}, \qquad \text{Eq.(5)}$$

where δ is the phase difference between the P and S components.

$$\text{First Polarizer} = \begin{bmatrix} \cos(P) & -\sin(P) \\ \sin(P) & \cos(P) \end{bmatrix}, \qquad \text{Eq.(6)}$$

where P is the azimuthal angle between the polarizer axis and the plane of incidence.

$$\text{Sample} = \begin{bmatrix} T_p & 0 \\ 0 & T_s \end{bmatrix}, \qquad \text{Eq.(7)}$$

where $T_{p,s}$ are the complex Fresnel coefficients for an isotropic sample.

$$ICE = \begin{bmatrix} ICE_p & 0 \\ 0 & ICE_s \end{bmatrix}, \qquad \text{Eq.(8)}$$

where $ICE_{p,s}$ are the pre-determined complex Fresnel coefficients for an isotropic ICE core.

$$\text{Second Polarizer} = \begin{bmatrix} 1 & 0 \\ 0 & 0 \end{bmatrix} \cdot \begin{bmatrix} \cos(A) & \sin(A) \\ -\sin(A) & \cos(A) \end{bmatrix}, \qquad \text{Eq.(9)}$$

where A is the azimuthal angle between the second polarizer axis and the plane of incidence.

Therefore, the output signal is a function of the first polarizer angle (P), second polarizer (i.e., analyzer) angle (A), pre-determined ICE Fresnel coefficients ($ICE_{p,s}$), and the sample Fresnel coefficients. With the first and second polarizers communicatively coupled to CPU station 24 via links A,B, the detector output signal can be solved for the sample Fresnel coefficients. Finally, CPU station 24 relates the sample Fresnel coefficients to the ellipsometric parameters, Ψ and Δ, from the ellipsometric definitions:

In Reflection: $\text{Tan}(\Psi)e^{i\Delta} = |R_p/R_s|$      Eq. (10), and

In Transmission: $\text{Tan}(\Psi)e^{i\Delta} = |T_p/T_s|$      Eq. (11).

Accordingly, and still referring to FIG. 2, in certain embodiments, sample 206 and optical element 204 may have different angular orientations in relation to one another. The box surrounding sample 206 is intended to illustrate how sample 206 and optical element 204 are positioned at different angles. For example, sample 206 may be oriented at non-normal incidence such that a distinction is made between the electric field vector that is parallel to the plane of incidence (i.e., P Polarized) and the component of the electric field vector that is perpendicular to the plane of incidence (i.e., S Polarized). At normal incidence, the electric field vector is coincident with the plane of incidence and there is no distinction between S and P polarized light. Thus, in order to measure the change in polarization after first polarized light 211 has interacted with sample 206 and optical element 204, the two components of the electric field vectors must be separated by transforming their projection on to the plane of incidence. As described above, the detected output (signal 228), along with the polarization states and polarizer angles detected at first and second polarizers 205,215 via links A,B, CPU station 24 determines the change in amplitude of the polarization, as well as the change in phase of the polarization.

Furthermore, in certain embodiments, in order to maximize the sensitivity of optical computing device 22 to measure the largest change in amplitude and phase of the polarization, sample 206 may be oriented at the Brewster angle. The Brewster angle may be defined as the angle of incidence where the reflected P polarized light reaches a minimum value. At this angle of incidence (i.e., Brewster angle), the difference between P polarized light and S polarized light is maximized and will therefore maximize the accuracy and sensitivity of the measurements since the ratio of these two components is measured by CPU station 24. In yet other embodiments, the difference between the angular orientations of sample 206 and optical element 204 may be at or substantially near the Brewster Angle.

The angular orientations of the first and/or second polarizers 205,215 may be altered in a variety of ways. The amount of light transmitted through the first or second polarizers 205,215 will depend on the angle, i.e., orientation relative to the electric field vector coming from sample 206 and optical element 204. In certain embodiments, the azimuthal angle of first polarizer 205 is fixed, while in others the azimuthal angle of first polarizer 205 may be rotating. In such embodiments, the first and second polarizers 205,215 may be operatively coupled to an actuation device (not shown) which rotates the polarizers to a desired angle. Mechanical or electrical rotational motors may be utilized as the actuation devices, in addition to a linear actuator in which linear motion is converted into rotational motion.

The angles of rotation may result in, for example, a pure P polarized light, pure S polarized light or an intermediate P and S polarized light. Alternatively, the actuation device may continuously rotate where not one defined polarized state is generated, but all of them over the course of one full rotation. For example, starting with pure P, then intermediate P and S, and then pure S polarized light. In other examples, the first polarizer 205 may be operatively coupled to the actuation device while second polarizer 215 is stationary. In other examples, first polarizer 205 may be fixed, while second polarizer 215 is coupled to the actuation device and, thus, rotates. As previously mentioned, the angular orientations of first and second polarizers 205,215 may be communicated to CPU station 24 via links A,B.

In yet other illustrative embodiments, first or second polarizers 205,215 may be polarization modulators that enable optical computing device 200 to dynamically switch between a pure P or S polarized light. In other embodiments, the azimuthal angular orientation of first and second polarizers 205,215 may be adjusted to nullify/extinguish the reflected/transmitted light, resulting in an alternative method by which to solve for Ψ and Δ. For example, nullification may be achieved here by rotating either first polarizer 205 or second polarizer 215, while keeping the other held fixed, until the light intensity at detector 216 is zero. CPU station 24 may then determine Ψ and Δ by allowing the left hand side of equation (4) be equal to zero and solving for Ψ and Δ.

Figure 3:
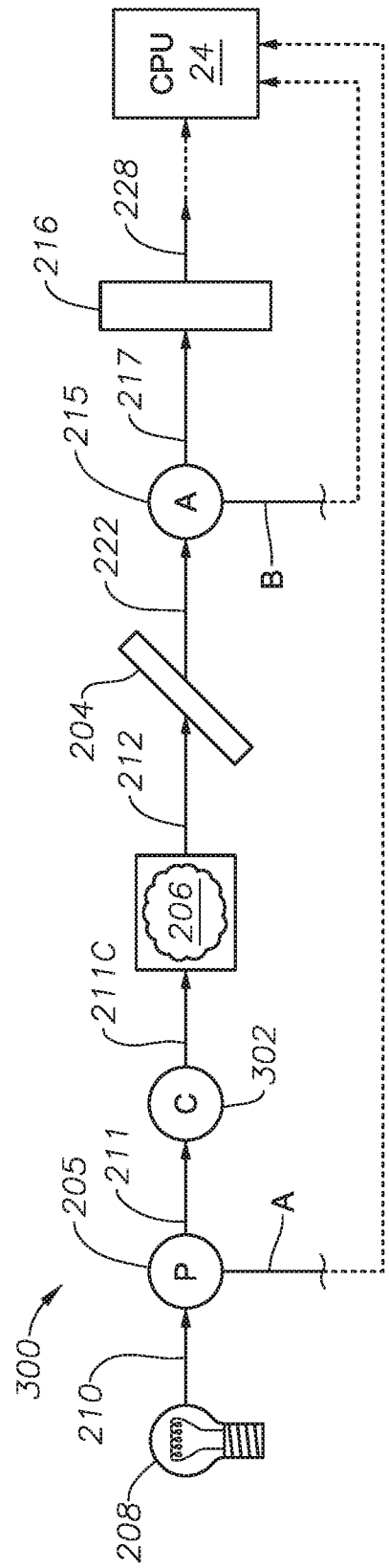
FIG. 3 is a block diagram of another intensity-independent optical computing device employing a compensator, according to certain illustrative embodiments of the present disclosure.

FIG. 3 illustrates a block diagram of yet another optical computing device 300 employing a rotating compensator, according to certain illustrative embodiments of the present disclosure. Optical computing device 300 is somewhat similar to optical computing device 200 described with reference to FIG. 2 and, therefore, may be best understood with reference thereto, where like numerals indicate like elements. In contrast to optical computing device 200, device 300 includes a rotating compensator 302 positioned to optically interact with first polarized light 211 to thereby generate a compensated first polarized light 211C. Rotating compensator 302 introduces a phase delay to the first polarized light 211 to thereby create circularly polarized light (i.e., compensated first polarized light 211C). Rotating compensator 302 is used to increase the accuracy of the measurement when the phase change of the reflected polarization, Δ, is near 0 and/or 180 degrees. This illustrative embodiment is beneficial if high resolution is needed for the regression vector for Δ approaching 0 to 180 degrees. In an alternative embodiment, however, the rotating compensator may be positioned after sample 206, wherein its operation will be understood by those ordinarily skilled in the art having the benefit of this disclosure.

Figure 4:
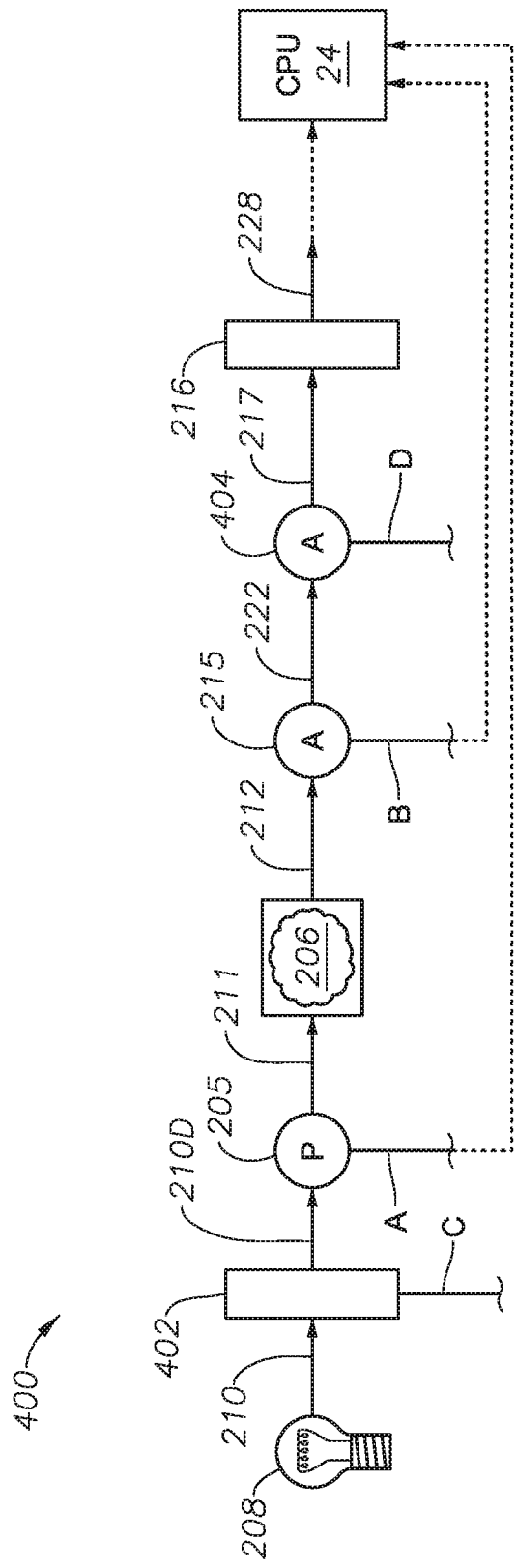
FIG. 4 is a block diagram of another intensity-independent optical computing device utilizing a second polarizer as the optical element, according to certain illustrative embodiments of the present disclosure.

FIG. 4 illustrates a block diagram of yet another optical computing device 400 employing second polarizer 215 as the optical element 204, according to certain illustrative embodiments of the present disclosure. Optical computing device 400 is somewhat similar to optical computing device 200 described with reference to FIG. 2 and, therefore, may be best understood with reference thereto, where like numerals indicate like elements. In contrast to optical computing device 200, device 400 does not include optical element 204. Instead, optical computing device 400 utilizes second polarizer 215 as the optical element, and includes a wavelength dispersive element 402 and third polarizer 404. Wavelength dispersive element 402 may be a variety of devices, such as, for example, a scanning monochromator, grating or prism.

During operation, electromagnetic radiation 210 optically interacts with wavelength dispersive element 402 so that the wavelength of dispersed electromagnetic radiation 210D is changed to coincide with the angle of second polarizer 215. Since CPU station 24 is rotating second polarizer 215 to a desired setting of Ψ and Δ for each wavelength, it is therefore also necessary to have only that wavelength of light incident on sample 206 and the polarizers at that time, thus the use of wavelength dispersive element 402 is needed. In this embodiment, the output of second polarizer 215 needs to be a specific, but different, value for each wavelength in the spectra. In order to do so, CPU station 24, via wavelength dispersive element 402, scans that specific wavelength and then rotates second polarizer 215 to produce the desired state for that wavelength. Then, CPU station 24 tunes wavelength dispersive element 402 to the next wavelength, and again changes the angle of second polarizer 215 accordingly.

After interacting with sample 206, sample-interacted light 212 is directed to second polarizer 215 which essentially acts as the ICE core in previous embodiments to generate optically-interacted light 222. In doing so, second polarizer 215 produces a spectroscopic polarization state that mimics the regression vector for the analyte of interest, as previously described herein. As previously described, CPU station 24 controls the angle of first polarizer 205 via link A; as a result, wavelength dispersive element 402 is also controlled by CPU station 24 via link C accordingly.

Thereafter, optically-interacted light 222 is directed to third polarizer 404 whereby the second polarization state is defined, as described in previous embodiments. Also, as in other embodiments, CPU station 24 is coupled to third polarizer 404 via link D so that the change in polarization between the first polarized light 211 and second polarized light 217 is determined, as well as to provide control of the angular orientation of third polarizer 404. Also, as previously described, CPU station 24 sends signals via links A,B to thereby program first and second polarizers 205,215 to rotate to the azimuthal angle necessary to produce the appropriate regression vector. Such an embodiment allows for a simpler optical computing device and ICE core since it eliminates the design and fabrication of an ICE core.

Figure 5B:
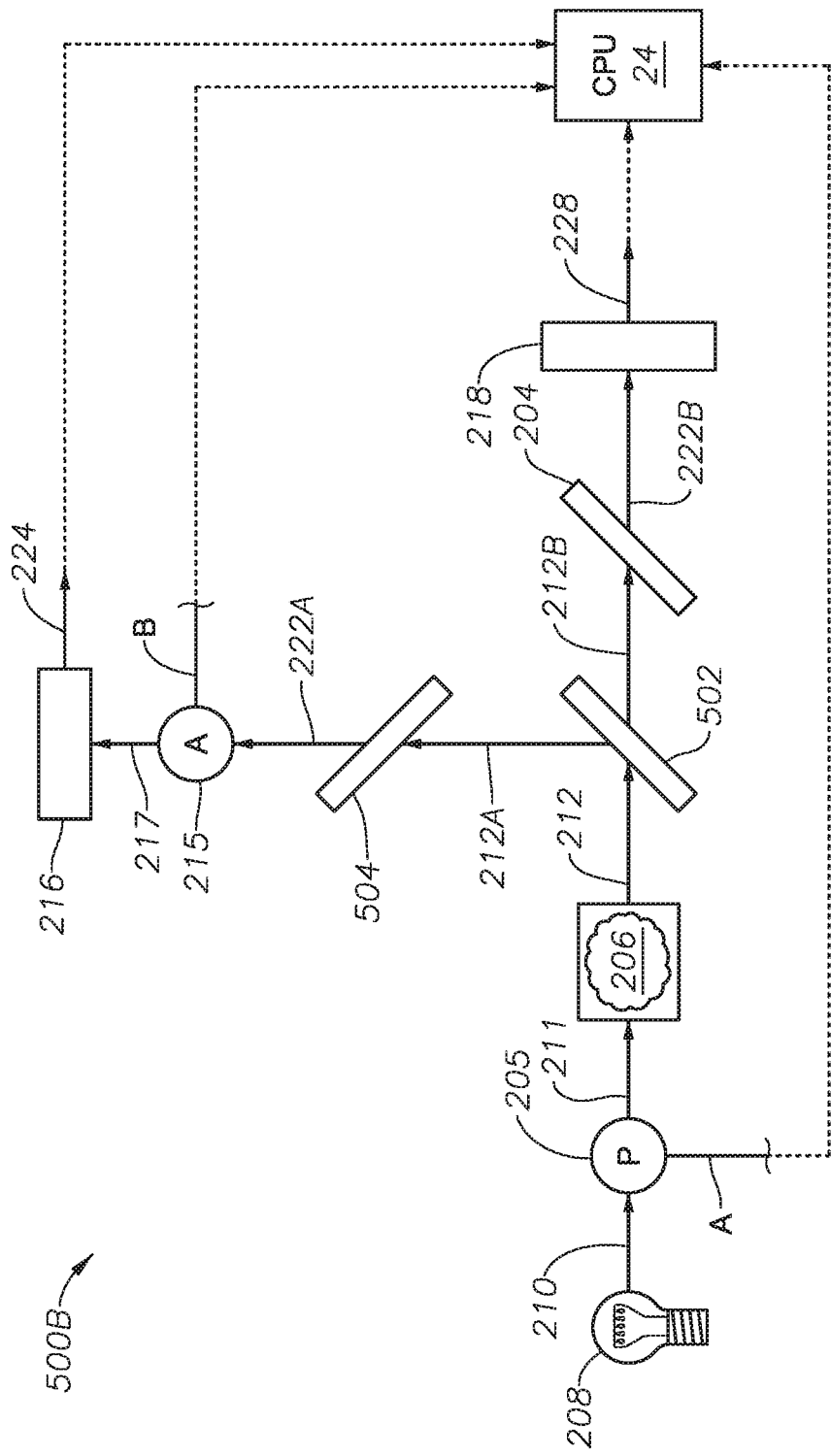

FIGS. 5A and 5B illustrate a block diagrams of yet other optical computing devices 500A and 500B employing a dual detector geometry, according to certain illustrative embodiments of the present disclosure. Optical computing devices 500A and 500B are somewhat similar to optical computing device 200 described with reference to FIG. 2 and, therefore, may be best understood with reference thereto, where like numerals indicate like elements. In contrast to optical computing device 200, device 500A includes a second detector 218, and optical element 204 also functions as a beam splitter whereby optically-interacted light portions 222A and 222B are directed to second polarizer 215 and detector 218, respectively. Although not shown, detectors 216,218 are communicably coupled to CPU station 24 (or an on-board processor). Output signals 228 and 226 are used to determine a first and second characteristic of sample 206. In this example, output signal 228 is utilized to extract Ψ and Δ as previously described, while output signal 226 is utilized to provide the intensity as with traditional devices. In this embodiment, reflection and transmission may be measured simultaneously for light intensity, Ψ and Δ. Such an embodiment may be utilized with any other embodiments described herein. This embodiment allows measurement of three observables, namely Ψ, Δ and intensity, which may be advantageous in measuring more than one analyte and/or increase measurement accuracy and confidence. In this embodiment, optical element 204 has been designed to target for intensity, Ψ and Δ.

In the alternate embodiment of FIG. 5B, optical computing device 500B includes a separate beam splitter 502 positioned to optically interact with sample-interacted light 212 to thereby split the light into sample-interacted light portions 212A and 212B. Sample-interacted light 212B is then directed to optical element 204 wherein it optically interacts therewith to generate second optically-interacted light 222B. At the same time, sample-interacted light 212A is then directed to a second optical element 504 (e.g., another ICE core) whereby it optically interacts to generate first optically-interacted light 222A. Second polarizer 215 then optically interacts with first optically-interacted light 222A to produce second polarized light 217. Thereafter, second polarized light 217 and second optically-interacted light 222B are detected by detectors 216 and 218, respectively. This embodiment allows measurement of three observables also, namely Ψ, Δ and intensity, which may be advantageous in measuring more than one analyte and/or increase measurement accuracy and confidence. In this embodiment, optical element 204 has been designed for intensity, while optical element 502 has been designed to target Ψ and Δ.

Those ordinarily skilled in the art having the benefit of this disclosure realize the aforementioned optical computing devices are illustrative in nature, and that there are a variety of other optical configurations which may be utilized. These optical configurations not only include the reflection, absorption or transmission methods described herein, but can also involve scattering (Raleigh & Raman, for example) as well as emission (fluorescence, X-ray excitation, etc., for example). In addition, the optical computing devices may comprise a parallel processing configuration whereby the sample-interacted light is split into multiple beams. The multiple beams may then simultaneously go through corresponding ICE cores and second polarizers, whereby multiple analytes of interest are simultaneously detected. The parallel processing configuration is particularly useful in those applications that require extremely low power or no moving parts. Moreover, one or more features of the embodiments described herein, may be combined as desired. Those ordinarily skilled in the art having the benefit of this disclosure will realize the choice of a specific optical configuration is mainly dependent upon the specific application and analytes of interest.

In addition to downhole or completion applications, the optical computing devices described herein may be utilized in a variety of others environments. Such environments may include, for example, those as diverse as those associated with surface and undersea monitoring, satellite or drone surveillance, pipeline monitoring, or even sensors transiting a body cavity such as a digestive tract. Within those environments, the optical computing devices may be utilized to detect sample characteristics in real-time.

Accordingly, embodiments and related methodologies of the present disclosure provide a number of advantages. The first, for example, is radiometric correction. Traditional optical computing devices require detailed radiometric analysis and measurements (e.g., detector wavelength sensitivity, source wavelength emissivity) to be completed on the optical components used in the system. Embodiments of the present disclosure, however, are not restrained to consider the impact of these components' spectroscopic intensity on the optical transmission properties of the ICE core and, enable the most accurate design, fabrication and implementation of the ICE core. As a result, the intensity-independent computing device would require fewer radiometric measurements and calibration schemes.

Second, through use of a compensator in certain embodiments, the ICE core is calibrated to accurately measure $\Psi$ and $\Delta$ at each wavelength. No further calibration of the computing device is needed. This type of calibration would also be independent of temperature. Third, traditional optical computing devices measure a single property using the intensity of light at each wavelength (in the sample and the ICE core itself). The intensity-independent computing devices of the present disclosure, however, will measure two or more of the intensity, $\Psi$ and $\Delta$ at each wavelength.

Fourth, for example, ICE cores seek to maximize the variance between the analyte and the matrix signals in a sample. This will occur in a spectroscopic wavelength range where the components are absorbing. Using the embodiments described herein, there can be unrelated spectroscopic regions outside of these absorbing regions that can be used dependently or complimentary of the absorbing regions. Fifth, the design and fabrication of intensity-independent ICE cores would lead to a simpler, thinner film stack. As a result, manufacturing costs and time would be saved. Sixth, $\Delta$ is more sensitive to very small concentrations of a substance in a matrix or solution, resulting in a more sensitive computing device. Seventh, low and/or fluctuating light conditions and scattering do not impact measurements, thereby resulting in a more dependable computing device.

Embodiments described herein further relate to any one or more of the following paragraphs:

1. An optical computing device to determine a characteristic of a sample, the optical computing device comprising: a first polarizer that optically interacts with electromagnetic radiation to produce first polarized light that optically interacts with a sample to produce sample-interacted light; a first optical element that optically interacts with the sample-interacted light to produce optically-interacted light which corresponds to a characteristic of the sample; a second polarizer that optically interacts with the optically-interacted light to produce second polarized light; and a first detector positioned to measure the second polarized light and thereby generate a first signal utilized to determine a first characteristic of the sample.

2. An optical computing device as defined in paragraph 1, wherein the sample and first optical element have different angular orientations in relation to one another.

3. An optical computing device as defined in any of paragraphs 1-2, wherein the different angular orientation is at or substantially near the Brewster Angle.

4. An optical computing device as defined in any of paragraphs 1-3, wherein: the first polarizer defines a first polarization state of the electromagnetic radiation; and the second polarizer is an analyzer that defines a second polarization state of the optically-interacted light representing a change in polarization between the first and second polarization states, wherein the change in polarization is utilized to determine the first characteristic of the sample.

5. An optical computing device as defined in any of paragraphs 1-4, wherein the change in polarization comprises a change in an amplitude or phase of the polarization states.

6. An optical computing device as defined in any of paragraphs 1-5, wherein the change in amplitude is represented by Tan $\Psi$=|Tp/Ts| or Tan $\Psi$=|Rp/Rs|.

7. An optical computing device as defined in any of paragraphs 1-6, wherein the change in phase is represented by $\Delta=\delta 1-\delta 2$.

8. An optical computing device as defined in any of paragraphs 1-7, further comprising an actuation device operatively coupled to at least one of the first or second polarizers to move the first or second polarizers through a full angular rotation that generates a pure P polarized light, pure S polarized light, and intermediate P and S polarized light.

9. An optical computing device as defined in any of paragraphs 1-8, wherein the first polarizer is operatively coupled to the actuation device; and the second polarizer is stationary.

10. An optical computing device as defined in any of paragraphs 1-9, wherein: the first polarizer is fixed; and the second polarizer is operatively coupled to the actuation device.

11. An optical computing device as defined in any of paragraphs 1-10, wherein the first polarizer is a polarization modulator.

12. An optical computing device as defined in any of paragraphs 1-11, further comprising a rotating compensator positioned to optically interact with the first polarized light in order to generate compensated first polarized light that optically interacts with the sample.

13. An optical computing device as defined in any of paragraphs 1-12, wherein the first optical element comprises a beam splitter, and the optical computing device further comprises a second detector positioned to measure the optically-interacted light and thereby generate a second signal utilized to determine a second characteristic of the sample.

14. An optical computing device as defined in any of paragraphs 1-13, further comprising: a beam splitter positioned between the sample and first optical element to thereby generate first and second portions of the sample-interacted light, wherein the first portion of the sample-interacted light is directed to the first optical element; a second optical element positioned to optically interact with the second portion of sample-interacted light to thereby generate second optically-interacted light; and a second detector positioned to measure the second optically-interacted light and thereby generate a second signal utilized to determine a second characteristic of the sample.

15. An optical computing device as defined in any of paragraphs 1-14, wherein: the first and second polarized lights comprise at least one of a P polarized light or S polarized light; and the first detector utilizes the P and S polarized lights to generate the first signal which corresponds to at least two characteristics of the sample, the at least two characteristics comprising: a characteristic corresponding to a change in amplitude of polarization between the first and second polarized lights; and a characteristic corresponding to a change in phase difference of polarization between the first and second polarized lights.

16. An optical computing device as defined in any of paragraphs 1-15, wherein the sample is at least one of a wellbore fluid, downhole tool or rock formation.

17. An optical computing device as defined in any of paragraphs 1-16, further comprising a signal processor communicably coupled to the first detector to computationally determine the characteristic of the sample in real-time.

18. An optical computing device as defined in any of paragraphs 1-17, wherein the first optical element is an Integrated Computational Element.

19. An optical computing device as defined in any of paragraphs 1-18, wherein the optical computing device comprises part of a downhole tool or wellbore.

20. A method utilizing an optical computing device to determine a characteristic of a sample, the method comprising: optically interacting electromagnetic radiation with a first polarizer to produce first polarized light; optically interacting the first polarized light with a sample to produce sample-interacted light; optically interacting a first optical element with the sample-interacted light to generate optically-interacted light which corresponds to a characteristic of the sample; optically interacting the optically-interacted light with a second polarizer to produce second polarized light; generating a first signal that corresponds to the second polarized light through utilization of a first detector; and determining a first characteristic of the sample using the first signal.

21. An optical computing method as defined in paragraph 20, further comprising positioning the sample and first optical element at different angular orientations in relation to one another.

22. An optical computing method as defined in any of paragraphs 20-21, wherein the different angular orientation is at or substantially near the Brewster Angle.

23. An optical computing method as defined in any of paragraphs 20-22, wherein: the first polarizer defines a first polarization state of the electromagnetic radiation; and the second polarizer is an analyzer that defines a second polarization state of the optically-interacted light representing a change in polarization between the first and second polarization states, wherein the change in polarization is utilized to determine the first characteristic of the sample.

24. An optical computing method as defined in any of paragraphs 20-23, wherein the change in polarization comprises a change in an amplitude or phase of the polarization states.

25. An optical computing method as defined in any of paragraphs 20-24, further comprising rotating at least one of the first or second polarizers to an angle of rotation; and generating at least one of a pure P polarized light, pure S polarized light, or an intermediate P and S polarized light.

26. An optical computing method as defined in any of paragraphs 20-25, further comprising switching the first or second polarized lights between a pure P or pure S polarized light using a polarization modulator.

27. An optical computing method as defined in any of paragraphs 20-26, further comprising introducing a phase delay to the first polarized light using a rotating compensator.

28. An optical computing method as defined in any of paragraphs 20-27, further comprising adjusting an angle of rotation of the first or second polarizers to thereby nullify an intensity of the second polarized light.

29. An optical computing method as defined in any of paragraphs 20-28, further comprising optically interacting a second detector with the optically-interacted light; and generating a second signal utilized to determine a second characteristic of the sample.

30. An optical computing method as defined in any of paragraphs 20-29, further comprising: optically interacting the sample-interacted light with a second optical element to produce second optically-interacted light; optically interacting a second detector with the second optically-interacted light; and generating a second signal utilized to determine a second characteristic of the sample.

31. An optical computing method as defined in any of paragraphs 20-30, wherein the first detector utilizes the P or S polarized lights to generate a signal which corresponds to at least two characteristics of the sample, the at least two characteristics comprising: a characteristic corresponding to a change in amplitude of polarization between the first and second polarized lights; and a characteristic corresponding to a change in phase difference of polarization between the first and second polarized lights.

32. An optical computing method as defined in any of paragraphs 20-31, wherein the first optical element is an Integrated Computational Element.

33. An optical computing method as defined in any of paragraphs 20-32, wherein the optical computing device is deployed in a wellbore.

34. An optical computing device to determine a characteristic of a sample, the optical computing device comprising a wavelength dispersive element positioned to optically interact with electromagnetic radiation to produce dispersed electromagnetic radiation; a first polarizer that optically interacts with the dispersed electromagnetic radiation to produce first polarized light that optically interacts with a sample to produce sample-interacted light; a second polarizer that optically interacts with the sample-interacted light to produce optically-interacted light that corresponds to a characteristic of the sample; a third polarizer that optically interacts with the optically-interacted light to produce second polarized light; and a detector positioned to measure the second polarized light and thereby generate a signal utilized to determine a characteristic of the sample.

35. An optical computing device as defined in paragraph 34, further comprising an actuation device operatively coupled to at least one of the first or second polarizers to move the first or second polarizers through an angular rotation that generates a pure P polarized light, pure S polarized light, and intermediate P and S polarized light.

36. An optical computing device as defined in any of paragraphs 34-35, wherein the sample and second polarizer have different angular orientations in relation to one another, the different angular orientation being at or substantially near the Brewster Angle.

37. An optical computing device as defined in any of paragraphs 34-36, wherein: the first polarizer defines a first polarization state of the electromagnetic radiation; and the third polarizer is an analyzer that defines a second polarization state of the optically-interacted light representing a change in polarization between the first and second polarization states, wherein the change in polarization is utilized to determine the characteristic of the sample.

38. An optical computing device as defined in any of paragraphs 34-37, wherein the change in polarization comprises a change in an amplitude or phase of the polarization states.

39. An optical computing device as defined in any of paragraphs 34-38, wherein the change in amplitude is represented by Tan $\Psi P=|Tp/Ts|$ or Tan $\Psi=|Rp/Rs|$.

40. An optical computing device as defined in any of paragraphs 34-39, wherein the change in phase is represented by $\Delta=\delta 1-\delta 2$.

41. An optical computing device as defined in any of paragraphs 34-40, wherein the first and second polarized lights comprise at least one of a P polarized light or S polarized light; and the detector utilizes the P and S polarized lights to generate the signal which corresponds to at least two characteristics of the sample, the at least two characteristics comprising: a characteristic corresponding to a change in amplitude of polarization between the first and second polarized lights; and a characteristic corresponding to a change in phase difference of polarization between the first and second polarized lights.

42. An optical computing device as defined in any of paragraphs 34-41, wherein the sample is at least one of a wellbore fluid, downhole tool or rock formation.

43. An optical computing device as defined in any of paragraphs 34-42, further comprising a signal processor communicably coupled to the first detector to computationally determine the characteristic of the sample in real-time.

44. An optical computing device as defined in any of paragraphs 34-43, wherein the optical computing device comprises part of a downhole tool or wellbore.

45. A method utilizing an optical computing device to determine a characteristic of a sample, the method comprising: optically interacting electromagnetic radiation with a wavelength dispersive element to produce dispersed electromagnetic radiation; optically interacting the dispersed electromagnetic radiation with a first polarizer to produce first polarized light; optically interacting the first polarized light with a sample to produce sample-interacted light; optically interacting the sample-interacted light with a second polarizer to produce optically-interacted light which corresponds to a characteristic of the sample; optically interacting the optically-interacted light with a third polarizer to produce second polarized light; optically interacting the second polarized light with a detector to generate a signal that corresponds to the characteristic of the sample; and determining the characteristic of the sample using the signal.

46. An optical computing method as defined in paragraph 45, further comprising rotating at least one of the first or second polarizers through a full angular rotation that generates a pure P polarized light, pure S polarized light, and intermediate P and S polarized light.

47. An optical computing method as defined in any of paragraphs 45-46, further comprising positioning the sample and second polarizer at different angular orientations in relation to one another, the different angular orientation being at or substantially near the Brewster Angle.

48. An optical computing method as defined in any of paragraphs 45-47, wherein: the first polarizer defines a first polarization state of the electromagnetic radiation; and the third polarizer is an analyzer that defines a second polarization state of the optically-interacted light representing a change in polarization between the first and second polarization states, wherein the change in polarization is utilized to determine the characteristic of the sample.

49. An optical computing method as defined in any of paragraphs 45-48, wherein the change in polarization comprises a change in an amplitude or phase of the polarization states.

50. An optical computing method as defined in any of paragraphs 45-49, further comprising rotating the first polarizer; and maintaining the second polarizer in a stationary position.

51. An optical computing method as defined in any of paragraphs 45-50, further comprising maintaining the first polarizer in a stationary position; and rotating the second polarizer.

52. An optical computing method as defined in any of paragraphs 45-51, further comprising variably changing the first or second polarized lights between a pure P or S polarized light using a polarization modulator.

53. An optical computing method as defined in any of paragraphs 45-52, further comprising introducing a phase delay to the first polarized light using a rotating compensator.

54. An optical computing method as defined in any of paragraphs 45-53, further comprising adjusting the angle of rotation of the first or second polarizers to thereby nullify an intensity of the second polarized light.

55. An optical computing method as defined in any of paragraphs 45-54 wherein the detector utilizes the P or S polarized lights to generate the first signal which corresponds to at least two characteristics of the sample, the at least two characteristics comprising a characteristic corresponding to a change in amplitude of polarization between the first and second polarized lights; and a characteristic corresponding to a change in phase difference of polarization between the first and second polarized lights.

56. An optical computing method as defined in any of paragraphs 45-55, wherein the optical computing device is deployed along a wellbore.

57. A method utilizing an optical computing device to determine a characteristic of a sample, the method comprising performing multivariate optical computing based on changes in polarization of the electromagnetic radiation to thereby determine one or more sample characteristics.

58. An optical computing method as defined in paragraph 57, wherein the change in polarization comprises a change in an amplitude or phase of polarization states.

59. An optical computing method as defined in any of paragraphs 57-58, wherein performing multivariate optical computing further comprises defining a first polarization state of the electromagnetic radiation using a first polarizer; optically interacting the electromagnetic radiation with a sample to generate sample-interacted light; optically interacting the sample-interacted light with an optical element to produce optically-interacted light that corresponds to a characteristic of the sample; defining a second polarization state of the optically-interacted light using a second polarizer, wherein the second polarization state represents a change in polarization between the first and second polarization states; and utilizing the change in polarization states to determine the characteristic of the sample.

60. An optical computing method as defined in any of paragraphs 57-59, further comprising positioning the sample and second polarizer at different angular orientations in relation to one another.

Although various embodiments and methodologies have been shown and described, the disclosure is not limited to such embodiments and methodologies, and will be understood to include all modifications and variations as would be apparent to one ordinarily skilled in the art. Therefore, it should be understood that the disclosure is not intended to be limited to the particular forms disclosed. Rather, the intention is to cover all modifications, equivalents and alternatives falling within the spirit and scope of the disclosure as defined by the appended claims.

What is claimed is:

1. An optical computing device to determine a characteristic of a sample, the optical computing device comprising:
   a first polarizer that optically interacts with electromagnetic radiation to produce first polarized light that optically interacts with a sample to produce sample-interacted light;
   a first optical element that optically interacts with the sample-interacted light to produce optically-interacted light which corresponds to a characteristic of the sample;
   a second polarizer that optically interacts with the optically-interacted light to produce second polarized light which corresponds to a first characteristic of the sample, wherein the first and second polarizers produce a polarization state that approximates a multivariate regression vector corresponding to the first characteristic of the sample; and
   a first detector positioned to measure the second polarized light and thereby generate a first signal utilized to determine the first characteristic of the sample.

2. The optical computing device as defined in claim 1, wherein the sample and first optical element have different angular orientations in relation to one another.

3. The optical computing device as defined in claim 2, wherein the different angular orientation is at or substantially near the Brewster Angle.

4. The optical computing device as defined in claim 1, wherein:
   the first polarizer defines a first polarization state of the electromagnetic radiation; and
   the second polarizer is an analyzer that defines a second polarization state of the optically-interacted light representing a change in polarization between the first and second polarization states, wherein the change in polarization is utilized to determine the first characteristic of the sample.

5. The optical computing device as defined in claim 4, wherein the change in polarization comprises a change in an amplitude or phase of the polarization states.

6. The optical computing device as defined in claim 5, wherein the change in amplitude is represented by:

$\tan \Psi = |T_p/T_s|$; or $\tan \Psi = |R_p/R_s|$.

7. The optical computing device as defined in claim 5, wherein the change in phase is represented by:

$\Delta = \delta_1 - \delta_2$.

8. The optical computing device as defined in claim 1, further comprising an actuation device operatively coupled to at least one of the first or second polarizers to move the first or second polarizers through a full angular rotation that generates a pure P polarized light, pure S polarized light, and intermediate P and S polarized light.

9. The optical computing device as defined in claim 8, wherein:
   the first polarizer is operatively coupled to the actuation device; and
   the second polarizer is stationary.

10. The optical computing device as defined in claim 8, wherein:
    the first polarizer is fixed; and
    the second polarizer is operatively coupled to the actuation device.

11. The optical computing device as defined in claim 1, wherein the first polarizer is a polarization modulator.

12. The optical computing device as defined in claim 1, further comprising a rotating compensator positioned to optically interact with the first polarized light in order to generate compensated first polarized light that optically interacts with the sample.

13. The optical computing device as defined in claim 1, wherein the first optical element comprises a beam splitter, and the optical computing device further comprises a second detector positioned to measure the optically-interacted light and thereby generate a second signal utilized to determine a second characteristic of the sample.

14. The optical computing device as defined in claim 1, further comprising:
    a beam splitter positioned between the sample and first optical element to thereby generate first and second portions of the sample-interacted light, wherein the first portion of the sample-interacted light is directed to the first optical element;
    a second optical element positioned to optically interact with the second portion of sample-interacted light to thereby generate second optically-interacted light; and
    a second detector positioned to measure the second optically-interacted light and thereby generate a second signal utilized to determine a second characteristic of the sample.

15. The optical computing device as defined in claim 1, wherein:
    the first and second polarized lights comprise at least one of a P polarized light or S polarized light; and
    the first detector utilizes the P and S polarized lights to generate the first signal which corresponds to at least two characteristics of the sample, the at least two characteristics comprising:
        a characteristic corresponding to a change in amplitude of polarization between the first and second polarized lights; and
        a characteristic corresponding to a change in phase difference of polarization between the first and second polarized lights.

16. The optical computing device as defined in claim 1, wherein the sample is at least one of a wellbore fluid, downhole tool or rock formation.

17. The optical computing device as defined in claim 1, further comprising a signal processor communicably coupled to the first detector to computationally determine the characteristic of the sample in real-time.

18. The optical computing device as defined in claim 1, wherein the first optical element is an Integrated Computational Element.

19. The optical computing device as defined in claim 1, wherein the optical computing device comprises part of a downhole tool or wellbore.

20. A method utilizing an optical computing device to determine a characteristic of a sample, the method comprising:
    optically interacting electromagnetic radiation with a first polarizer to produce first polarized light;
    optically interacting the first polarized light with a sample to produce sample-interacted light;

optically interacting a first optical element with the sample-interacted light to generate optically-interacted light which corresponds to a characteristic of the sample;

optically interacting the optically-interacted light with a second polarizer to produce second polarized light which corresponds to a first characteristic of the sample, wherein the first and second polarizers produce a polarization state that approximates a multivariate regression vector corresponding to the first characteristic of the sample;

generating a first signal that corresponds to the second polarized light through utilization of a first detector; and determining the first characteristic of the sample using the first signal.

21. The optical computing method as defined in claim 20, further comprising positioning the sample and first optical element at different angular orientations in relation to one another.

22. The optical computing method as defined in claim 21, wherein the different angular orientation is at or substantially near the Brewster Angle.

23. The optical computing method as defined in claim 20, wherein:
   the first polarizer defines a first polarization state of the electromagnetic radiation; and
   the second polarizer is an analyzer that defines a second polarization state of the optically-interacted light representing a change in polarization between the first and second polarization states, wherein the change in polarization is utilized to determine the first characteristic of the sample.

24. The optical computing method as defined in claim 23, wherein the change in polarization comprises a change in an amplitude or phase of the polarization states.

25. The optical computing method as defined in claim 20, further comprising:
   rotating at least one of the first or second polarizers to an angle of rotation; and
   generating at least one of a pure P polarized light, pure S polarized light, or an intermediate P and S polarized light.

26. The optical computing method as defined in claim 20, further comprising switching the first or second polarized lights between a pure P or pure S polarized light using a polarization modulator.

27. The optical computing method as defined in claim 20, further comprising introducing a phase delay to the first polarized light using a rotating compensator.

28. The optical computing method as defined in claim 20, further comprising adjusting an angle of rotation of the first or second polarizers to thereby nullify an intensity of the second polarized light.

29. The optical computing method as defined in claim 20, further comprising:
   optically interacting a second detector with the optically-interacted light; and
   generating a second signal utilized to determine a second characteristic of the sample.

30. The optical computing method as defined in claim 20, further comprising:
   optically interacting the sample-interacted light with a second optical element to produce second optically-interacted light;
   optically interacting a second detector with the second optically-interacted light; and
   generating a second signal utilized to determine a second characteristic of the sample.

31. The optical computing method as defined in claim 20, wherein the first detector utilizes the P or S polarized lights to generate a signal which corresponds to at least two characteristics of the sample, the at least two characteristics comprising:
   a characteristic corresponding to a change in amplitude of polarization between the first and second polarized lights; and
   a characteristic corresponding to a change in phase difference of polarization between the first and second polarized lights.

32. The optical computing method as defined in claim 20, wherein the first optical element is an Integrated Computational Element.

33. The optical computing method as defined in claim 20, wherein the optical computing device is deployed in a wellbore.

* * * * *